Figure 1:
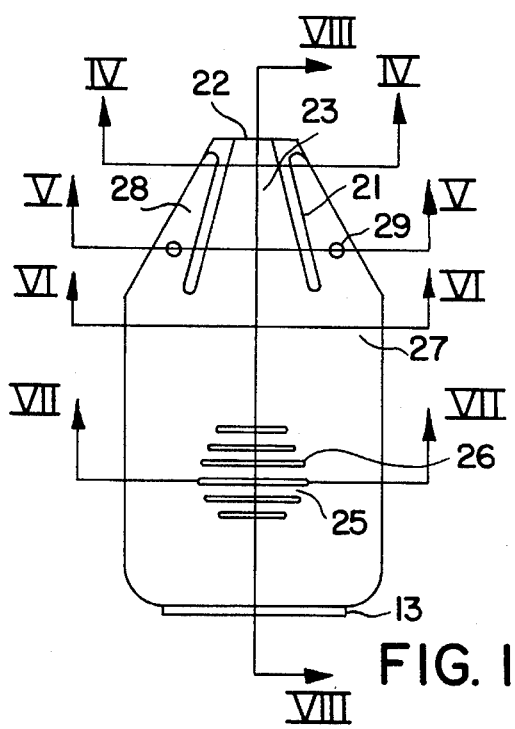

United States Patent [19]
Prause

[11] Patent Number: 5,460,299
[45] Date of Patent: Oct. 24, 1995

[54] DISPENSER FOR DISPENSING A LIQUID CONTAINER IN A PLASTIC BAG AND A PLASTIC BAG FOR USE IN THE DISPENSER

[75] Inventor: Jan U. Prause, Copenhagen, Denmark

[73] Assignee: Eva Willadsen, Holte, Denmark

[21] Appl. No.: 319,568

[22] Filed: Oct. 7, 1994

[51] Int. Cl.$^6$ .................................................. B65D 37/00
[52] U.S. Cl. ............................................ 222/213; 222/494
[58] Field of Search ................................... 222/105, 212, 222/213, 420, 494

[56] References Cited

U.S. PATENT DOCUMENTS

| | | | |
|---|---|---|---|
| 3,063,601 | 11/1962 | Hertz | 222/213 |
| 3,179,301 | 4/1965 | Lucht | 222/213 |
| 3,685,700 | 8/1972 | Martin | 222/213 |

*Primary Examiner*—Gregory L. Huson
*Attorney, Agent, or Firm*—Kerkam, Stowell, Kondracki & Clarke; Edward J. Kondracki

[57] ABSTRACT

Dispenser for dispensing a liquid, in particular a drug, such as for instance eye drops, which dispenser comprises two half portions which can be assembled by means of a snap lock to form a closed chamber adapted to surround a plastic bag containing the liquid, said bag having a constricted portion into which the reservoir of the bag extends, the constricted portion forming a neck with a dosage duct, through which the liquid, after breaking of the constricted portion, may be squeezed by compression of the plastic bag, one wall of the chamber of the dispenser being resilient to such an extent that the plastic bag can be compressed, and the dispenser comprising a shut off for sealing the dosage opening when no liquid is to be supplied. With the object of making the closing means open simultaneously with the compression of the dispenser for squeezing out liquid from the dispenser, the means for sealing the dosage opening are a pair of pincers formed by the two half portions, said pair of pincers being adapted to compress the constricted portion of the plastic bag close to the discharge opening of the dosage duct, at least on one of the half portions of the dispenser the pincers being extended into a ridgid tongue-shaped area of the resilient portion of the wall of the chamber and being supported for performing a seesaww motion together with the pincers when pressure is applied on the tongue-shaped area.

11 Claims, 1 Drawing Sheet

DISPENSER FOR DISPENSING A LIQUID CONTAINER IN A PLASTIC BAG AND A PLASTIC BAG FOR USE IN THE DISPENSER

The present invention relates to a dispenser for dispensing a liquid, in particular a drug, such as for instance eye drops, which dispenser comprises two half portions which can be assembled by means of a snap lock to form a closed chamber adapted to surround a plastic bag containing the liquid, said bag having a constricted portion into which the reservoir of the bag extends, the constricted portion forming a neck with a dosage duct, through which the liquid, after breaking of the constricted portion, may be squeezed by compression of the plastic bag, one wall of the chamber of the dispenser being resilient to such an extent that the plastic bag can be compressed, and said dispenser comprising means for sealing the dosage opening when no liquid is to be supplied. The invention also relates to a plastic bag for use in the dispenser.

It is common knowledge that eye-drops must be sterile at the time of application. It is therefore usual to distribute such drugs in comparatively small packages in form of closable bottles with a dropper mechanism, the content of which corresponds to the consumption during a treatment period. If the treatment covers several days, it is necessary to preserve the content of the package by adding preservatives. However, most of the preservatives that can be used are damaging to the eye, just as they may give allergic reactions. Besides, the content cannot with certainty be reckoned to be sterile by the end of the treatment.

Disposable packages for eye-drops intended to be used within a short time, for instance 24 hours, are known. As the content is to be used so quickly, it is justifiable to avoid preservation, and consequently, the damaging effect of preservatives to the eye of the patient is avoided.

However, these known disposable packages suffer from severe drawbacks which limit their use. The drug becomes on account of the price of the package comparatively costly compared to the same drug on bigger package units, and often, the package cannot be closed again. In practice, the package cannot be manufactured with so small a content that it only contains one exactly measured dosage.

These conditions in combination have the undesirable effect that many patients use the content of the disposable packages—without closing the package again—for dispensing several dosages with the purpose of saving money during the treatment. This may both be due to meanness, poverty or lack of information (developing countries) and entails an unacceptably great risk of infection, which is caused by the failure to close the lid in combination with the non-use of preservation.

The above drawbacks may induce conjunctivititis or other similiar diseases, but the drawbacks are, however, particularly serious in case of patients who are being treated for lack of lachrymal fluid and who need life-long treatment.

These problems can be overcome by a kind of closable package which contains a small number of dosages and which is provided with a closing arrangment which does not entail an obvious risk of infection of the content of the package, when the drug is used over a period of a few days. The present invention is based on the perception that a combination of a plastic bag, which can be manufactured economically, and a closable dispenser surrounding the plastic bag and containing suitable means for closing the package, may eliminate the above problems.

Such a package is known in connection with a dispenser for lubricating oil for locks and similar mechanisms. The package consists of a plastic bag with a neck with a dosage duct seam-welded thereto at the end, said duct being breakable by cutting or tearing. The plastic bag is after opening placed in the dosage duct of the dispenser, which is adapted to surround or protect the plastic bag and which is provided with a connecting piece provided with a screw cap, in which the dosage duct discharges. After removal of the cap the dispenser is operated thereby that the walls of the chamber containing the plastic bag is squeezed together, the content of the plastic bag being squeezed out of the plastic bag through the dosage duct discharging in the connecting piece. The known dispenser is, however, not able to reduce the risk of infection of the content, as the screw cap is an evident carrier of bacteria and may transfer microorganisms from a previous plastic bag to the next one, when the content of the former has been used.

The object of the invention is to provide a dispenser which is sealed automaticly after each dosage and which minimizes the risk of transferring microroganisms from an emptied plastic bag to the next one inserted in the dispenser. It is further the object to provide a dispenser, which during use may be operated with one hand only.

This object is according to the invention met thereby that the dispenser is characteristic by the subject matter of the characterizing clause of claim 1.

The dispenser is provided with a pair of pincers consisting of two half portions which, when no liquid is dispensed, compress the dosage duct close to its discharge opening. When handling the dispenser during the dispensing of a dosage the user compresses the chamber, but at the same time the support provided in the wall of the half portion causes the pair of pincers to open. Thereby a dispenser has been provided which only opens the dosage duct for the short periods, in which the dispenser is handled with a view to dosing the liquid. As the dosage duct is closed by compression and the discharge opening established by tearing off the tip of the plastic bag is not touched, the risk of infection of the content of the plastic bag is minimal. The dispenser can, therefore, be used securely in connection with plastic bags containing sufficient liquid for a whole day's consumption or maybe two–three days' consumption and may be re-used for dosing a number of plastic bags which contains a sufficient amount of drug for a treatment covering several weeks. As the pressure applied to the finger grips on the dispenser both opens the pincers and exerts a pressure on the plastic bag the dispenser may be operated by one hand leaving the other hand free for holding the eye lids open. When the pressure on the finger grips is released the pincers close the discharge opening by means of the resiliancy of the support.

According to a preferred embodiment of the invention, the pair of pincers in the supported half portion has a width only slightly exceeding the width of the dosage duct, while the pair of pincers in the other half portion is substantially wider and comprises fixing means for the bag. This embodiment ensures a correct positioning of the constricted portion of the dosage duct in relation to the pair of pincers in such a way that the dosage duct is correctly closed.

The fixation may advantageously be established as stated in claim 3. If the plastic bag in the area adjacent the dosage duct comprises flaps along the seam-welding of the plastic foil, the holes for the fixation may be placed in these areas.

In order to keep the plastic bag on the pins and to protect the part of the pair of pincers which compresses the dosage duct, the supported half portion may comprise a pair of arms extending from each side of the pair of pincers and abutting against the wider part of the other half portion.

It is particularly advantageous that the pins are the male part of a snap lock, the female part of which is placed in the other half portion, preferably in the extended arms. The fixing means thereby contribute to holding the two half portions together and to effectively preventing the plastic bag from displacing itself in relation to the pair of pincers taking care of the closing.

According to a preferred embodiment of the invention the two half portions opposite the pair of pincers may be connected by means of an integral foil hinge. This embodiment makes it practically impossible to mishandle the dispenser when exchanging the plastic bag.

To facilitate the dosing and to make the pair of pincers open sufficiently irrespective of whether the plastic bag is completely filled or partially emptied, the chamber may according to the invention be filled with a resilient, compressible foam material.

Finally, it is practical in order to instruct the user about how to hold the dispenser during use that the tongue-shaped area of the flexible wall is provided with transverse ribs or other indications of a finger grip.

Furthermore, the invention relates to a plastic bag for use in the dispenser according to claim 1. The plastic bag is characterized by the subject matter of claims 9 and 10. The plastic bag comprises seam-weldings which are placed and kept in the contact area between the two half portions of the dispenser. By letting the reservoir of the bag be of the same shape and size as the chamber of the dispenser, an excess pressure will be created in the bag when the dispenser is compressed to open the pair of pincers, whereby liquid is squeezed out through the dosage duct.

By letting the plastic bag have the same outline as the dispenser, sufficiently wide welding flaps will be provided in the area adjacent the dosage duct for the holes used for the fixation without any risk arising that they may puncture the reservoir of the package.

Figure 2:
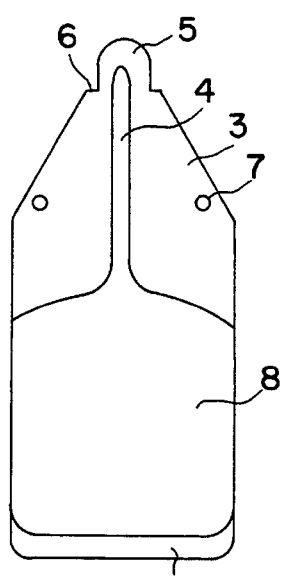
Figure 3:
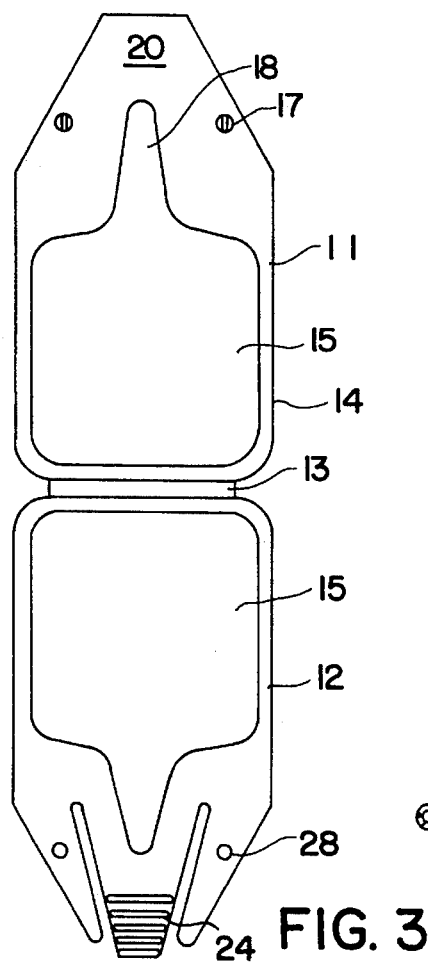
Figure 4:
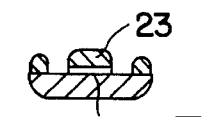
Figure 5:
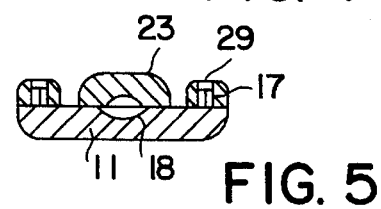
Figure 6:
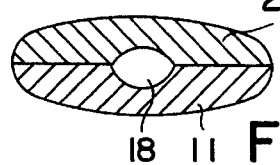
Figure 7:
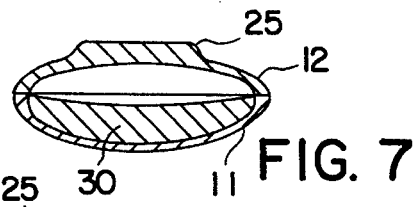
Figure 8:
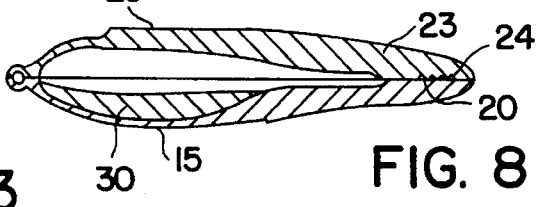

The invention will be described in detail in the following with reference to the drawing, in which:

FIG. 1 is a plane view of an embodiment of the dispenser according to the invention, FIG. 2 shows a plastic bag suitable for use in the dispenser according to claim 1, FIG. 3 shows the dispenser according to FIG. 1 in its open position and with a visible inner surface, FIGS. 4–8 show sectional views through the dispenser according to FIG. 1 along the lines marked by corresponding Roman numerals.

FIG. 1 of the drawing shows a plane view of an embodiment of a dispenser according to the invention. The dispenser consists in the embodiment shown of a container comprising two hinged half portions with flexible plastic walls. The two half portions are shown in open condition in FIG. 3. The dispenser is adapted to be closable around a plastic bag corresponding to the one shown in FIG. 2, the two hinged half portions being clipsed together by means of one or more snap locks. In the closed condition it is possible—as will be explained in the following—by compressing the flexible walls of the dispenser firstly to open the means of the dispenser for closing the dosage duct of the plastic bag, secondly to squeeze some droplets out of the package by compressing the flexible walls.

The plastic bag shown in FIG. 2 is made from a tube of plastic foil. The tube is at one end closed by means of a transverse seam-welding 2, in which two layers of foil face one another on the same level. At the other end the foil tube is likewise seam-welded, but the weldings 3 extend over a bigger length and from two sides towards the centre line of the package forming a neck, in which the welded portions are separated by a constricted, non-welded area 4 forming a dosage duct. The two weldings do, however, converge and create a closing tip 5 of the dosage duct 4. The plastic bag is at its end with the weldings 4 cut off with an outline corresponding to the one shown in FIG. 2. A particularly constricted portion 6 is provided in the area 5, from which portion the dosage duct extends. This portion 6 makes it possible, for instance by cutting, to open the dosage duct 4, when the content of the plastic bag is to be used. The two welding zones 3 may be provided with holes, by means of which the plastic bag may be fixated in the dispenser as will be explained in detail in the following. Between the weldings the reservoir 8 of the plastic bag is provided, in which reservoir fluid, for instance eye-drops, may be contained and from which, after breaking of the package by cutting the portion 6, fluid may be squeezed out through the dosage duct 4 by compression of the reservoir 8.

The dispenser, which is generally named 10, is shown in its open condition in FIG. 3. It consists of two half portions 11 and 12 mutually connected by means of a hinge, which may in practice be an integral foil hinge, the two half portions being connected by a thin-walled area 13. The dispenser 10 is manufactured for instance by injection moulding from a plastic material which on one hand is sufficiently soft and resilient to impart a considerable flexibility to the two half portions in the areas with comparatively small wall-thickness, but yet on the other hand so rigid that the areas with increased wall-thickness acquire a reasonable rigidity and dimensional stability. The two half portions comprise a border area 14 with increased wall-thickness and rigidity and a wall portion 15 with a recess having a comparatively small wall-thickness and considerable flexibility. The wall portions 15 surrounds a chamber which holds the reservoir 8 of the plastic bag. When inserting the plastic bag, the weldings 3 are placed on top of a tapering area 16 of the half portion 11. In this area a pair of pins 17 is provided, said pins fitting exactly in the holes 7. The pins are to a certain degree undercut and divided by means of a notch, thus forming the male part of a snap lock. The constricted area has a comparatively big wall-thickness and consequently a considerable rigidity. An extension 18 of the groove 15 extends into this area with a view to making room for the dosage duct 4. However, the extension 18 does not extend all the way to the front edge 19 of the half portion, but leaves a plane area 20 along the inside of the edge 19. The outer contour of the half portion corresponds to the shape of the bag apart from the area 6, which, when the bag is placed in the dispenser, protrudes outside the front edge 19.

The second half portion 12 has a similar groove 15 and an outer contour corresponding to that of the first half portion. However, the second half portion is provided with some additional supports and some recesses, which together form the closing means for the dosage duct 4, when the dispenser is closed around the plastic bag 1. These supports can be seen most distinctly from FIG. 1 which shows the dispenser in its closed position and the half portion 12 facing the user. The half portion 12 has two recesses 21 extending from the front edge 22 of the half portion towards the border of the groove 15. Between the recesses a pair of pincers 23 is formed, said pair of pincers being somewhat wider than the duct 4 of the bag. In order to make them ridgid the pair of pincers has increased thickness compared with the wall portion 15 surrounding the chambers holding the reservoir 8. The pincers are extended with increased thickness into a tongue-shaped area 25 of the wall portion holding the reservoir of the plastic bag. A support 27 with increased thickness is provided across the pincers in the area between the pincers and the tongue-shaped extension, the supprt forming a combined pivot and biasing means for the seesaw formed by the pincers and the tongue-shaped extension 25. The extension is preferably provided with rifles 26 forming a finger grip, which is to be pressed when using the dispenser. The support 27 extends to the border area of the dispenser and is in contact with the second half portion 11 for transfer of the pressure exerted on the finger grip during the seesaw movement of the pincers and their extension when pressure is applied on the finger grip 26. By pressing the finger grip 25 two things happen simultaneously, namely firstly that the pair of pincers 23 and the finger grip 26 makes a seesaw or rocking motion, thereby lifting the protrusions 24 from the dosage duct 4, and secondly that a pressure is exerted on the reservoir of the plastic bag which is surrounded by the flexible walls 15. Now some drops of the liquid in the reservoir may be dispensed, and when the dosing is sufficient, the pressure on the finger grip is eased, whereby the pair of pincers 23 returns to its original position, in which it presses the protrusions 24 towards the area 20 of the second half portion, the dosage duct being once more compressed and closed.

The recesses 21 define a pair of arms 28 receiving the pins for locking of the two half portions. For this purpose the arms are provided with a pair of holes 29 adapted to receive the pins 17 and designed as the male part of the snap lock. The arms 28 secure, together with the constricted area 16 on the other half portion 11, the plastic bag in the dispenser in such a way that the dosage duct is always positioned opposite the pair of pincers 23 and consequently effectively sealed off, when the protrusions 24 rest against the area 20.

FIGS. 4–8 show sectional views through the dispenser. The positioning of the sectional views in FIG. 1 is indicated by Roman numerals corresponding to the numbers of the figures. The chamber shown in FIG. 7 and surrounded by the walls 15 may according to an embodiment of the invention be partly filled with a resilient foam material 30. The foam contributes to the squeezing out of liquid from the reservoir 8 of the plastic bag, which can then be compressed without the flexible walls of the chamber being completely pressed against each other.

As the dispenser effectively seals off the plastic bag, when no liquid is dispensed, and as it does not have any areas getting in contact with the liquid during dosing, the possibility of microorganisms infecting the content of the plastic bag will be considerably reduced. Consequently, a dispenser with an accompanying disposable bag has been created, by means of which it has become possible to dispense a non-preserved drug in a number of dosages over a period of one day or a few days. This makes the dispenser particularly suited for dosing of for instance lachrimal fluid to patients who are themselves unable to produce such fluid. Such a treatment may be for life, and it is therefore important that it is acceptable from an economic point of view but also without potential risk of allergy or infection in the patient.

In order to investigate the extent of bacterial contamination that appear in disposable plastic foil envelopes containing unpreserved eye drops after the opening of the envelope a number of tests have been made.

Ten plastic foil envelopes, each containing 15 ml unpreserved, sterile, isotonic saline solution for use with contact lenses, were opened with a pair of scissors. A few drops of saline solution were pressed out of each envelope directly on a sterile agar culture medium. After opening each envelope was closed by means of an ordinary clothes-peg, which pressed the sides of the opening together without touching the internal sides of the opening. Two envelopes were left undisturbed for 12 hours, two envelopes had culture samples taken every 4 hours on agar for 12 hours, two envelopes had culture samples taken every 2 hours on agar for 12 hours, two envelopes had culture samples taken on agar every hour for 12 hours and two envelopes had culture samples taken every ½ hour on agar for 12 hours. Growth of bacteria was measured and identified in accordance with normal routine procedures at the microbiological lab. Eye Pathology Institute, University of Copenhagen. None of the of the samples fron the envelopes induced growth of bacteria even after 10 days.

It is concluded that the sealing mechanism in the dispenser according to the invention will be adequate to prevent retrograde bacterial invasion into the eye drops kept in the plastic bag of the dispenser.

Both the plastic bag and the dispenser may within the scope of the invention be designed in other ways, the combined effect being still attained. The plastic bag may alternatively consist of two separate foils which are welded by a circumferential seam-welding. Through this embodiment an improved fixation of the plastic bag in the dispenser may be attained, the bag being, if desired, securable along the entire periphery of the two half portions.

In the embodiment described only one of the half portions is provided with recesses for defining a pair of pincers. Alternatively, both half portions may be provided with incisions defining a pair of pincers which opens by exertion of a pressure on the finger grips. In this embodiment the dispenser will be symmetrical around the hinged region, which will facilitate the adjustment of the mutual rigidity of the two half portions. The two half portions may besides be hinged in other ways than by means of a foil hinge. Moreover, they may be completely separated and maybe identical, the assembling taking place also at the end provided with a hinge, for instance by means of a snap lock. In this case the snap locks are to be placed in pairs symmetrically about the longitudinal axis of the dispenser and with male and female parts.

We claim:

1. Dispenser for dispensing a liquid, in particular a drug, such as for instance eye drops, which dispenser comprises two half portions which can be assembled by means of a snap lock to form a closed chamber adapted to surround a plastic bag containing the liquid, said bag having a reservoir and a constricted portion into which the reservoir of the bag extends, the constricted portion forming a neck with a dosage duct, through which the liquid, after breaking of the constricted portion, may be squeezed by compression of the plastic bag, one wall of the chamber of the dispenser being resilient to such an extent that the plastic bag can be compressed, and said dispenser comprising means for sealing the dosage opening when no liquid is to be supplied, characterized in that the means for sealing the dosage opening are a pair of pincers formed by the two half portions, said pair of pincers being adapted to compress the constricted portion of the plastic bag close to the discharge opening of the dosage duct, at least on one of the portions of the dispenser the pincers being extended into a rigid tongue-shaped area of the resilient portion of the wall of the chamber and being supported for performing a seesaw motion together with the wall, when a pressure is applied on the tongue-shaped area.

2. Dispenser according to claim 1, wherein the pincer in the supported half portion has a width only slightly exceeding the width of the dosage duct, while the pincer in the other half portion is substantially wider and comprises fixing means for the bag.

3. Dispenser according to claim 2, wherein the fixing means comprise pins adapted to be inserted in corresponding holes in the bag.

4. Dispenser according to claim 3, wherein the supported half portion comprises a pair of arms extending from each side of the pincer and abutting against the wider part of the other half portion.

5. Dispenser according to claim 4, wherein the pins are the male part of a snap lock, the female part of which is placed in the other half portion, preferably in the extended arms.

6. Dispenser according to claim 1, wherein the two half portions opposite the pair of pincers are connected by an integral foil hinge.

7. Dispenser according to claim 1, wherein the chamber is at least partially filled with a resilient, compressible foam material.

8. Dispenser according to claim 1, wherein the tongue-shaped area of the flexible wall is provided with transverse ribs or other indications of a finger rest.

9. Bag for use in a dispenser according to claim 1, characterized in that the bag is welded from a foil by means of seam-welding, in which two layers of foil face one another on the same level, and in which the size and the shape of the reservoir substantially correspond to the chamber in the dispenser, and in which at least part of the seam-welding/weldings is adapted to be fastened between the two half portions of the dispenser in at least a part of the periphery.

10. A bag for use in a dispenser according to claim 3, wherein the bag is welded from a foil by means of seam-welding, in which two layers of foil face one another on the same level, and in which the size and the shape of the reservoir substantially correspond to the chamber in the dispenser, and in which at least part of the seam-welding/weldings is adapted to be fastened between the two half portions of the dispenser in at least part of the periphery.

11. The bag according to claim 10, wherein the seam-welding in the area along the neck in the constricted portion has substantially the same outline as the dispenser and is provided with fixation holes corresponding to the pins placed in the dispenser.

* * * * *

UNITED STATES PATENT AND TRADEMARK OFFICE
CERTIFICATE OF CORRECTION

PATENT NO. : 5,460,299
DATED : Oct. 24, 1995
INVENTOR(S) : Jan U. PRAUSE

It is certified that error appears in the above-indentified patent and that said Letters Patent is hereby corrected as shown below:

Title Page [54], in the title, and col. 1, line 2, the word "CONTAINER" should be
-- CONTAINED --.

Title Page [57], in the ABSTRACT:

Line 21 of ABSTRACT: "ridgid" should be
-- rigid --.
Line 23 of ABSTRACT: "seesaww" should be
-- seesaw --.

Signed and Sealed this

Twenty-fourth Day of September, 1996

Attest:

BRUCE LEHMAN

*Attesting Officer*  *Commissioner of Patents and Trademarks*